(12) United States Patent
Hong et al.

(10) Patent No.: US 6,956,091 B2
(45) Date of Patent: Oct. 18, 2005

(54) ORGANIC ANTI-REFLECTIVE POLYMER AND PREPARATION THEREOF

(75) Inventors: Sung-eun Hong, Seongnam-shi (KR); Min-ho Jung, Icheon-shi (KR); Ki-ho Baik, Icheon-shi (KR)

(73) Assignee: Hyundai Electronics Industries Co., Ltd. (KR)

( * ) Notice: Subject to any disclaimer, the term of this patent is extended or adjusted under 35 U.S.C. 154(b) by 146 days.

(21) Appl. No.: 10/438,531

(22) Filed: May 14, 2003

(65) Prior Publication Data

US 2003/0208018 A1 Nov. 6, 2003

Related U.S. Application Data

(63) Continuation of application No. 09/603,485, filed on Jun. 23, 2000, now abandoned.

(30) Foreign Application Priority Data

Jun. 26, 1999 (KR) ........................................ 1999-24469

(51) Int. Cl.$^7$ ............................................. C08F 124/00
(52) U.S. Cl. ........................................ 526/273; 526/287
(58) Field of Search .................................. 526/273, 287

(56) References Cited

U.S. PATENT DOCUMENTS

| 4,424,270 A | 1/1984 | Erdmann et al. |
| 4,822,718 A | 4/1989 | Latham et al. |
| 5,674,648 A | 10/1997 | Brewer et al. |

FOREIGN PATENT DOCUMENTS

| EP | 0 277 038 | 1/1988 |
| GB | 1 442 346 | 7/1976 |
| GB | 2 115 422 A | 9/1983 |
| WO | WO 89/11511 | 11/1989 |
| WO | WO 00/01752 | 1/2000 |

OTHER PUBLICATIONS

Abstract No. 115:233228.
Abstract No. 103:179091.
Abstract No. 97:129167.
Abstract No. 97:14800.
Abstract No. 80:83887.
Abstract No. 124:118223.
Abstract No. 120:218596.
Abstract No. 116:31562.
Abstract No. 85:125647.

*Primary Examiner*—Bernard Lipman
(74) *Attorney, Agent, or Firm*—Townsend and Townsend and Crew LLP

(57) ABSTRACT

The present invention relates to organic anti-reflective coating polymers suitable for use in a semiconductor device during a photolithograhy process for forming ultrafine patterns using 193 nm ArF beam radiation, and preparation method therefor. Anti-reflective coating polymers of the present invention contain a monomer having a pendant phenyl group having high absorbency at the 193 nm wavelength. When the polymers of the present invention are used in an anti-reflective coating in a photolithography process for forming ultrafine patterns, the polymers eliminate the standing waves caused by changes in the thickness of the overlying photosensitive film, by the spectroscopic property of lower layers on wafer and by changes in CD due to diffractive and reflective light originating from the lower layers. Use of the anti-reflective coating of the present invention results in the stable formation of ultrafine patters suitable for 64M, 256M, 1G, 4G and 16G DRAM semiconductor devices and a great improvement in the production yield.

The present invention also relates to anti-reflective coating compositions containing these polymers and to the anti-reflective coatings formed from these compositions, as well as preparation methods therefor.

44 Claims, No Drawings

ORGANIC ANTI-REFLECTIVE POLYMER AND PREPARATION THEREOF

CROSS-REFERENCE TO RELATED APPLICATIONS

This application is a continuation of U.S. patent application Ser. No. 09/603,485, filed Jun. 23, 2000, now abandoned.

This application is related to Korean Patent Application No. 1999-24469 filed Jun. 26, 1999, and takes priority from that date.

BACKGROUND OF THE INVENTION

1. Field of the Invention

The present invention relates to an organic anti-reflective coating ("ARC") material which allows the stable formation of ultrafine patterns suitable for 64 M, 256 M, 1 G, 4 G and 16 G DRAM semiconductor devices. More particularly, the present invention relates to an organic anti-reflective coating material that contains a chromophore with high absorbance at the wavelengths useful for submicrolithography. A layer of said anti-reflection material can prevent back reflection of light from lower layers or a surface of the semiconductor ship, as well as eliminate the standing waves in the photoresist layer, during a submicrolithographic process using a 193 nm ArF laser light sources. Also, the present invention is concerned with an anti-reflective coating composition comprising such a material, an anti-reflective coating therefrom and a preparation method thereof

2. Description of the Prior Art

During a submicrolithographic process, one of the most important processes for fabricating highly integrated semiconductor devices, there inevitably occur standing waves and reflective notching of the waves due to the optical properties of lower layers coated on the wafer and to changes in the thickness of the photosensitive film applied thereon. In addition, the submicrolithographic process generally suffers from a problem of the CD (critical dimension) being altered by the diffracted light and reflected light from the lower layers.

To overcome these problems, it has been proposed to introduce a film, called an anti-reflective coating, between the substrate and the photosensitive film to prevent light reflection from the lower layer. Largely, anti-reflective coatings are classified into "organic" and "inorganic" by the materials used and into "absorbing" and "interfering" by the operation mechanisms.

An inorganic anti-reflective coating is used mainly in the process of ultrafine-pattern formation using i-line radiation with a wavelength of 365 nm. TiN and amorphous carbon have been widely used in light-absorbing coatings, and SiON has been used in light-interfering coatings. The SiON anti-reflective coatings are also adopted for submicrolithographic processes that use KrF light sources.

Recently, extensive and intensive research has been and continues to be directed to the application of organic anti-reflective coatings for such submicrolithography. In view of the present development status, organic anti-reflective coatings, if they are to be useful, must satisfy the following fundamental requirements:

First, during the pattern formation process, the photoresist must not be peeled from the substrate by dissolving in the solvent used in the organic anti-reflective coating. For this reason, the organic anti-reflective coating needs to be designed to form a cross-linked structure, and must not produce chemicals as a by-product.

Second, acid or amine compounds must not migrate in or out of the anti-reflective coating. This is because there is a tendency for undercutting at the lower side of the pattern if an acid migrates, and for footing if a base such as an amine migrates.

Third, the anti-reflective coating must have a faster etching speed compared to the photoresist layer so that the etching process can be performed efficiently by utilizing the photoresist layer as a mask.

Finally, the organic anti-reflective coatings should be as thin as possible while playing an excellent role in preventing light reflection.

As various as anti-reflective coatings are, those which are satisfactorily applicable for submicrolithographic processes using ArF light have thus far not been found. As for inorganic anti-reflective coatings, there have been reported no materials which can control interference at the ArF wavelength, that is, 193 nm. In contrast, active research has been undertaken to develop organic materials into superb anti-reflective coatings. In fact, in most cases of submicrolithography, the coating of photosensitive layers is necessarily followed by organic anti-reflective coatings that prevent the standing waves and reflective notching occurring upon light exposure, and that eliminate the influence of the back diffraction and reflection of light from lower layers. Accordingly, the development of such an anti-reflective coating material showing high absorption properties against specific wavelengths is one of the hottest and most urgent issues in the art.

SUMMARY OF THE INVENTION

The present invention overcomes the problems encountered in the prior art and provides a novel organic compound that can be used as an anti-reflective coating useful for submicrolithography processes using 193 nm ArF laser.

The present invention provides a method for preparing an organic compound that prevents the diffusion and reflection caused by light exposure in submicrolithography.

The present invention further provides an anti-reflective coating composition containing such a diffusion/reflection-preventive compound and a preparation method therefor.

The present invention also provides an anti-reflective coating formed from such a composition and a preparing method thereof.

The polymers of the present invention comprise a monomer with a phenyl group having high absorbance at 193 nm, so that the polymer resin absorbs 193 nm wavelength light. A cross-linking mechanism using a ring opening reaction is introduced into preferred polymer resins of the invention by adding another monomer having an epoxy structure, so that a cross-linking reaction takes place when coatings of the polymer resins are "hard baked", i.e., heated at a temperature of 100–300° C. for 10–1,000 seconds. Accordingly, a great improvement can be effected in the formation, tightness and dissolution properties of the anti-reflective coatings using polymers of the present invention. Particularly, maximal cross-linking reaction efficiency and storage stability are realized by the present invention. The anti-reflective coating resins of the present invention have superior solubility in all hydrocarbon solvents, in order to form a coating composition, yet are of such high solvent resistance after hard baking that they are not dissolved in any solvent at all. These advantages allow the resins to be coated without any problem to form an anti-reflective coating which prevents undercutting and footing problems when images are formed on the overlying photosensitive layer. Furthermore, coatings made of the acrylate polymers of the invention are higher in etch rate than the photosensitive film coatings, thereby improving the etch selection ratio therebetween.

DETAILED DESCRIPTION OF THE INVENTION

Polymer resins according to the present invention are represented by the following general formula 1:

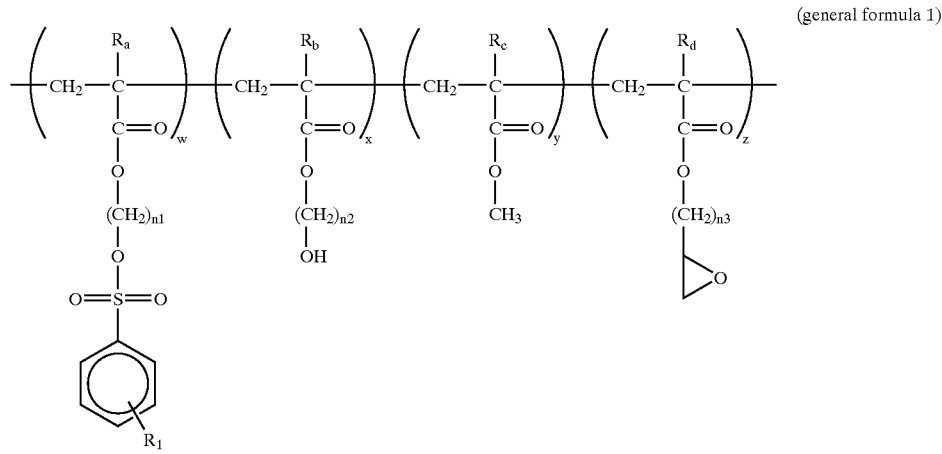

(general formula 1)

wherein, $R_a$, $R_b$, $R_c$ and $R_d$ each represents hydrogen or methyl group;

$R_1$ represents hydrogen, hydroxy, a substituted or unsubstituted, straight or branched $C_1$–$C_5$ alkyl, cycloalkyl, alkoxyalkyl or cycloalkoxyalkyl;

w, x, y and z each represents a mole fraction of 0.01–0.99; and $n_1$, $n_2$ and $n_3$ each represents an integer of 1 to 4;

and by the following general formula 2:

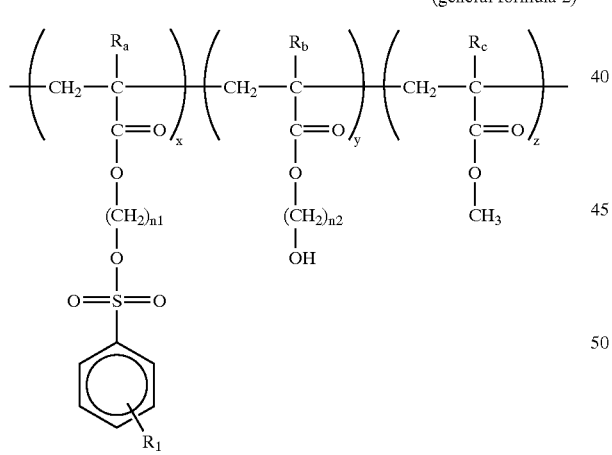

(general formula 2)

wherein, $R_a$, $R_b$, and $R_c$ each represents hydrogen or methyl group;

$R_1$ represents hydrogen, hydroxy, substituted or unsubstituted, straight or branched $C_1$–$C_5$ alkyl, cycloalkyl, alkoxyalkyl or cycloalkoxyalkyl;

x, y and z each represents mole fraction of 0.01–0.99; and $n_1$ and $n_2$ each represents an integer of 1 to 4.

The polymer resins of the present invention are particularly suitable for use as organic anti-reflective coatings because they comprise a (toluene-4-sulfonyloxy)alkyl acrylate monomer, in which the phenyl group readily absorbs wavelength of 193 nm. Preferred monomers comprise a monomer of the following chemical formula 3:

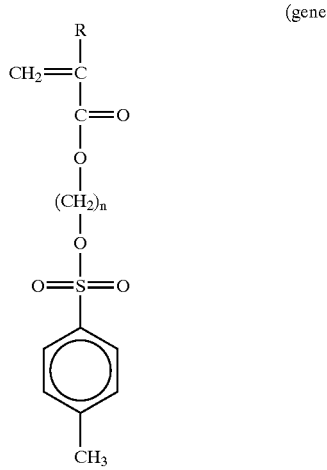

(general formula 3)

wherein,

R is hydrogen or methyl group; n is an integer of 2 or 3.

The polymers represented by general formula 1 can be prepared in accordance with the reaction equation 1 set forth below, wherein (toluene-4-sulfonyloxy)alkyl acrylate type monomers, hydroxyalkyl acrylate-type monomers, methyl acrylate-type monomers and glycidyl methacrylate-type monomers are polymerized with the aid of an initiator in a solvent. Each of the monomers has a mole fraction ranging from 0.01 to 0.99.

(reaction equation 1)

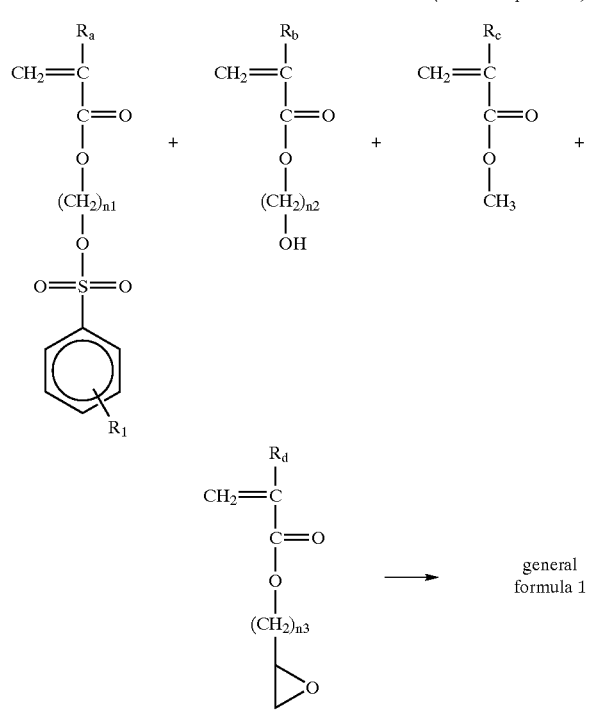

wherein, $R_a$, $R_b$, $R_c$ and $R_d$ each represents hydrogen or methyl group;

$R_1$ represents hydrogen, hydroxy, straight or branched $C_1$–$C_5$ alkyl, cycloalkyl, alkoxyalkyl or cycloalkoxyalkyl; and $n_1$, $n_2$ and $n_3$ each represents an integer of 1 to 4.

The polymers represented by general formula 2 above can be prepared in accordance with the reaction equation 2 set forth below, wherein, (toluene-4-sulfonyloxy)alkyl acrylate type monomers, hydroxyalkyl acrylate-type monomers and methyl acrylate-type monomers are polymerized with the aid of an initiator in a solvent. Each of the monomers has a mole fraction ranging from 0.01 to 0.99.

(reaction equation 2)

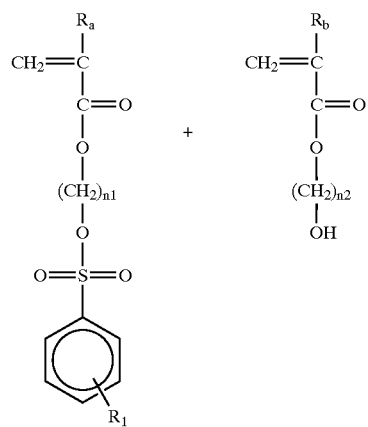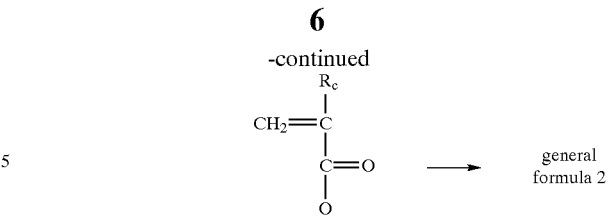

wherein, $R_a$, $R_b$, and $R_c$ each represents hydrogen or methyl group;

$R_1$ represents hydrogen, hydroxy, a substituted or unsubstituted, straight or branched $C_1$–$C_5$ alkyl, cycloalkyl, alkoxyalkyl or cycloalkoxyalkyl; and $n_1$ and $n_2$ represents an integer of 1 to 4.

Conventional radical initiators, preferably 2,2-azobisisobutyronitrile (AIBN), acetylperoxide, laurylperoxide or t-butylperoxide, may be used for initiating the polymerization reaction forming the polymers of general formulas 1 and 2. Also, conventional solvents may be used for the polymerization, preferably tetrahydrofuran, toluene, benzene, methylethylketone or dioxane. Preferably, the polymerization for the polymers of the general formulas 1 and 2 is carried out at 50–80° C.

Semiconductor devices of the present invention may be prepared as described below. The copolymer of general formula 1 or formula 2 may be dissolved in a suitable solvent alone, or with a cross-linker additive selected from acrolein, diethylacetal and melamine-type cross linkers, at an amount of 0.1 to 30% by weight. The solution is filtered and coated on a wafer and then hard-baked to form a cross-linked anti-reflective coating. Semiconductor devices can then be fabricated therefrom in the conventional manner.

Conventional organic solvents may be used in preparing the anti-reflective coating composition, with preference given to ethyl 3-ethoxypropionate, methyl 3-methoxy propionate, cyclohexanone or propyleneglycol methyletheracetate. The solvent is preferably used at an amount of 200 to 5000% by weight based on the weight of the anti-reflective coating resin copolymer used.

It has been found that the anti-reflective coatings of the present invention exhibit high performance in photolithography processes for forming ultrafine-patterns using 193 nm ArF radiation. The same was also true of where 248 nm KrF, 157 nm $F_2$ laser, E-beams, EUV (extremely ultraviolet) and ion beams are used as light sources.

A better understanding of the present invention may be obtained from following examples, which are set forth to illustrate, but are not to be construed to limit, the present invention.

EXAMPLE I

Synthesis of 2-(toluene-4-sulfonyloxy)ethyl acrylate monomer

To 0.35 mole of triethylamine was added 0.35 mole p-toluene sulfonylchloride followed by 0.3 mole of 2-hydroxyethyl acrylate The reaction mixture was stirred for over 24 hours with cooling, and monitored by TLC. The reaction mixture was neutralized with 1N sulfuric acid and washed with deionized water. The aqueous layer was extracted, and the organic layer were combined, dried over $MgSO_4$ to yield compound of chemical formula 1. The yield was 90–95%.

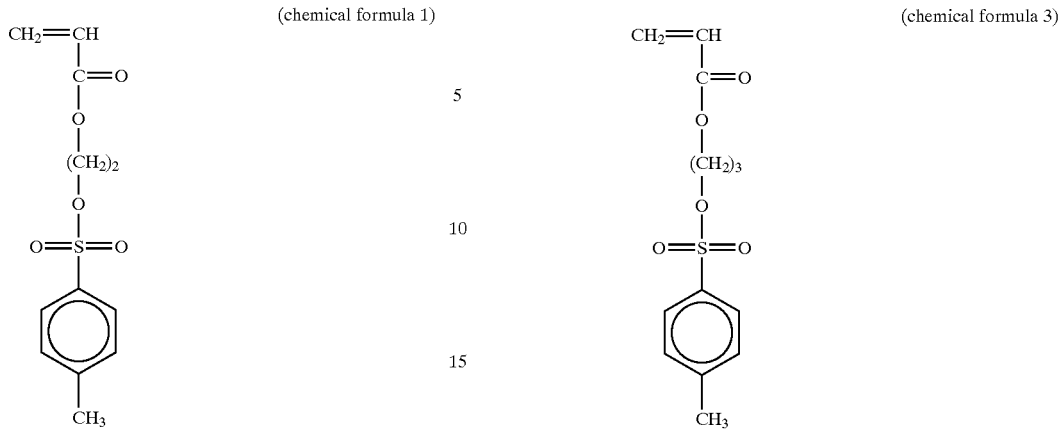

(chemical formula 1)

EXAMPLE II

Synthesis of 2-(toluene-4-sulfonyloxy)ethyl methacrylate monomer

To 0.35 mole of triethylamine was added 0.35 mole of p-toluene sulfonylchloride followed by 0.3 mole of 2-hydroxyethyl methacrylate. The reaction mixture was stirred for over 24 hours with cooling and monitored by TLC. The reaction mixture was neutralized with 1N sulfuric acid and washed with deionized water. The aqueous layer was extracted, and the organic layers were combined, dried over $MgSO_4$ to yield compound of chemical formula 2. The yield was 90–95%.

(chemical formula 2)

EXAMPLE III

Synthesis of 3-(toluene-4-sulfonloxy)propyl acrylate monomer

To 0.35 mole of triethylamine was added 0.35 mole of p-toluene sulfonylchloride followed by 0.3 mole of 3-hydroxypropyl acrylate. The reaction mixture was stirred for 24 hours with cooling and monitored by TLC. The reaction mixture was neutralized with 1N sulfuric acid and washed with deionized water. The aqueous layer was extracted, and the organic layers were combined and dried over $MgSO_4$ to provide compound of chemical formula 3. The yield was 90–95%.

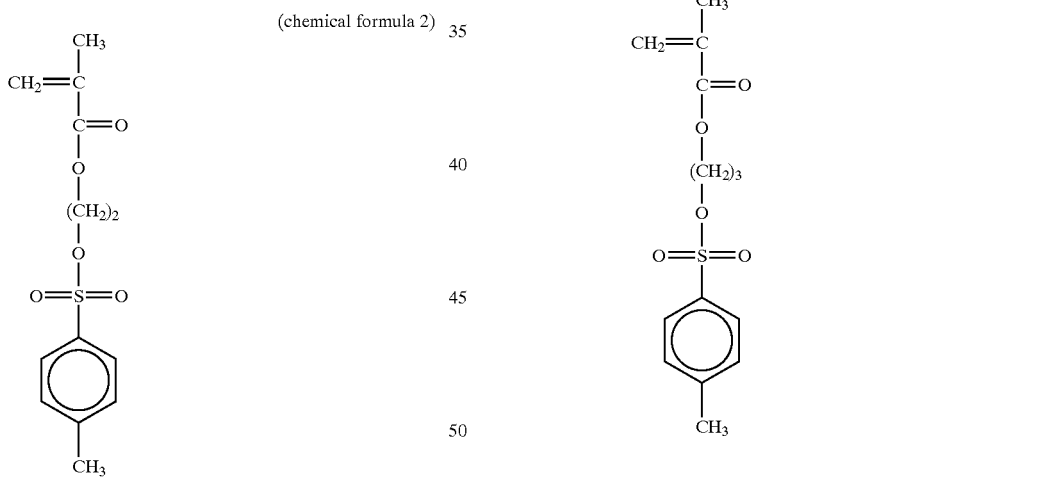

(chemical formula 3)

EXAMPLE IV

Synthesis of 3-(toluene-4-sulfonyloxy)propyl methacrylate monomer

To 0.35 mole of triethylamine was added 0.35 mole of p-toluene sulfonylchloride followed by 0.3 mole of 3-hydroxypropyl methacrylate. The reaction mixture was stirred for over 24 hours with cooling, and the reaction was monitored by TLC. The reaction mixture was neutralized with 1N sulfuric acid and washed with deionized water. The aqueous layer was extracted, and the organic layers were combined and dried over $MgSO_4$ to provide compound of chemical formula 4. The yield was 90–95%.

(chemical formula 4)

EXAMPLE V

Synthesis of poly [2-(toluene-4-sulfonyloxyl)ethyl acrylate/2-hydroxyethyl acrylate/-methyl methacrylate/-glycidyl methacrylate]

In a 500 ml round-bottom flask was placed 0.3 mole of 2-(toluene-4-sulfonyloxy)ethyl acrylate, 0.25 mole of 2-hydroxyethyl acrylate, 0.1 mole of methyl methacrylate, 0.3 mole of glycidyl methacrylate, 300 g of tetrahydrofuran (THF), and 0.1 g–3 g of 2,2-azobisisobutyronitrile (AIBN). The reaction mixture was heated to 60–75° C. for 5–20 hours. The product was precipitated in ethyl ether or n-hexane, filtered and dried to provide poly [2-(toluene-4-sulfonyloxyl)ethyl acrylate-/2-hydroxyethyl acrylate/-methyl methacrylate/-glycidyl methacrylate] represented by the following chemical formula 5, at a yield of 65–70%.

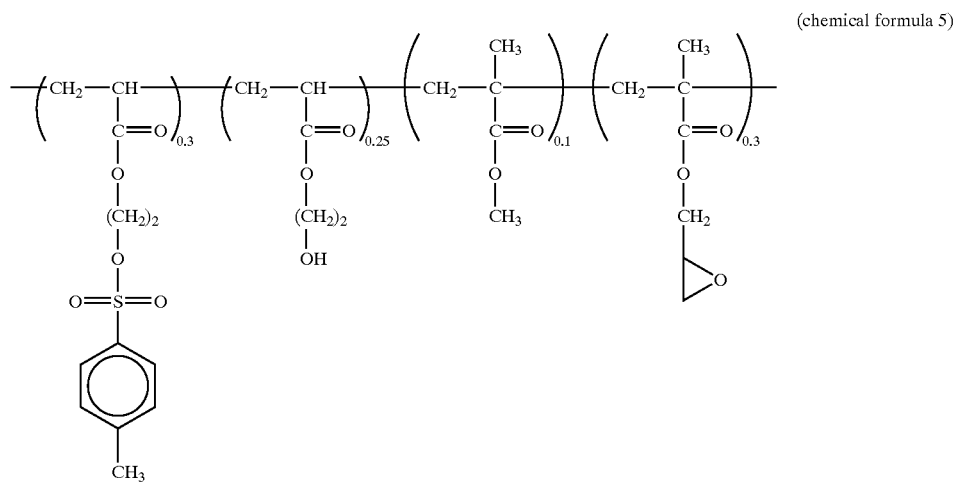

(chemical formula 5)

EXAMPLE VI

Synthesis of poly [2-(toluene-4-sulfonyloxy)ethyl acrylate/2-hydroxyethyl methacrylate/-methyl methacrylate/-glycidyl methacrylate]

In a 500 ml round-bottom flask was placed 0.33 mole of 2-(toluene-4-sulfonyloxy)ethyl acrylate, 0.2 mole of 2-hydroxyethyl methacrylate, 0.15 mole of methyl methacrylate, 0.3 mole of glycidyl methacrylate, 300 g of tetrahydrofuran (THF), and 0.1 g–3 g of AIBN. The reaction mixture was heated at 60–75° C. for 5–20 hours. The product was precipitated in ethylether or n-hexane, filtered and dried to provide poly [2-(toluene-4-sulfonyloxy)ethyl acrylate/2-hydroxyethyl methacrylate/-methyl methacrylate/-glycidyl methacrylate] represented by the following chemical formula 6, at a yield of 65–70%.

EXAMPLE VII

Synthesis of poly [2-(toluene-4-sulfonyloxy)ethyl acrylate/3-hydroxypropyl acrylate/-methyl methacrylate/-glycidyl methacrylate]

In a 500 ml round-bottom flask was placed 0.3 mole of 2-(toluene-4-sulfonyloxy)ethyl acrylate, 0.25 mole of 3-hydroxypropyl acrylate, 0.1 mole of methyl methacrylate, 0.3 mole of glycidyl methacrylate, 300 g of tetrahydrofuran (THF), and 0.1 g–3 g of AIBN. The reaction mixture was heated at 60–75° C. for 5–20 hours. The product precipitated in ethyl ether or n-hexane, filtered and dried to provide poly [2-(toluene-4-sulfonyloxy)ethyl acrylate/3-hydroxypropyl acrylate/-methyl methacrylate/-glycidyl methacrylate] represented by the following chemical formula 7, at a yield of 65–70%.

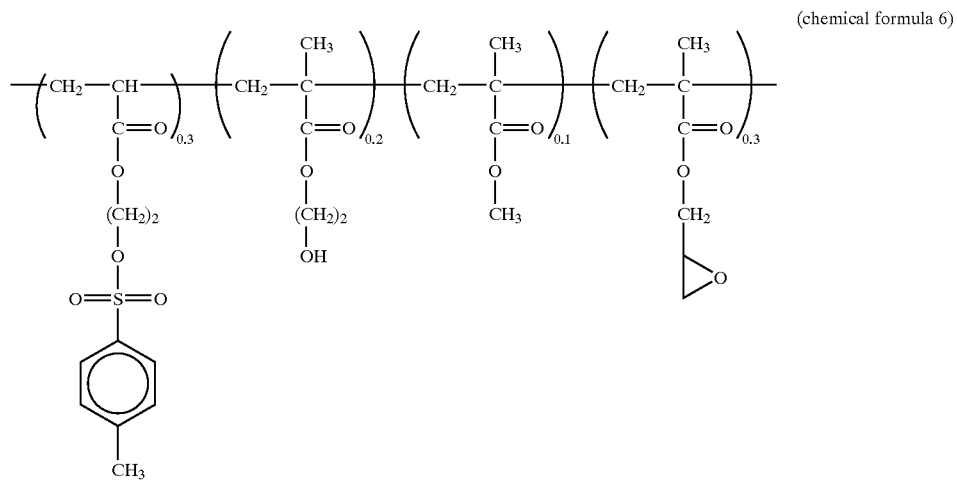

(chemical formula 6)

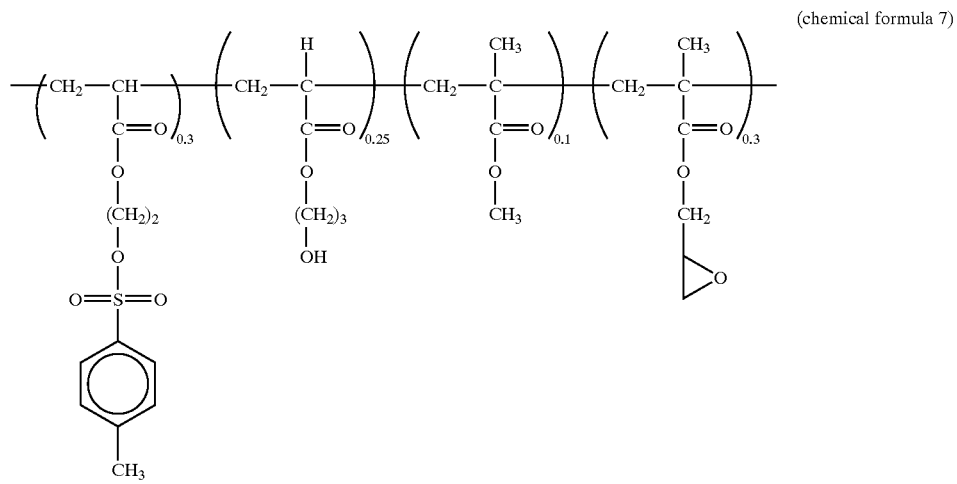

(chemical formula 7)

EXAMPLE VIII

Synthesis of poly [2-(toluene-4-sulfonyloxy)ethyl acrylate/3-hydroxypropyl methacrylate-/methyl methacrylate-/glycidyl methacrylate]

In a 500 ml round-bottom flask was placed 0.3 mole of 2-(toluene-4-sulfonyloxy)ethyl acrylate, 0.23 mole of 3-hydroxypropyl methacrylate, 0.1 mole of methyl methacrylate, 0.3 mole of glycidyl methacrylate, 300 g of tetrahydrofuran (THF), and 0.1 g–3 g of AIBN. The reaction mixture was heated at 60–75° C. for 5–20 hours. The product was precipitated in ethyl ether or n-hexane, filtered and dried to provide poly [2-(toluene-4-sulfonyloxy)ethyl acrylate/3-hydroxypropyl methacrylate-/methyl methaclylate-/glycidyl methacrylate] represented by the following chemical formula 8, at a yield of 65–70%.

EXAMPLE IX

Synthesis of poly [2-(toluene-4-sulfonyloxy)ethyl acrylate/4-hydroxybutyl acrylate/-methyl methacrylate/-glycidyl methacrylate]

In a 500 ml round-bottom flask was placed 0.3 mole of 2-(toluene-4-sulfonyloxy)ethyl acrylate, 0.2 mole of 4-hydroxybutyl acrylate, 0.1 mole of methyl methacrylate, 0.3 mole of glycidyl methacrylate, and 300 g of tetrahydrofuran (THF), and 0.1 g–3 g of AIBN. The reaction mixture was heated at 60–75° C. for 5–20 hours. The product was precipitated in ethyl ether or n-hexane, filtered and dried to provide poly [2-(toluene-4-sulfonyloxy)ethyl acrylate/4-hydroxybutyl acrylate/-methyl methacrylate/-glycidyl methacrylate] represented by the following chemical formula 9, at a yield of 65–70%.

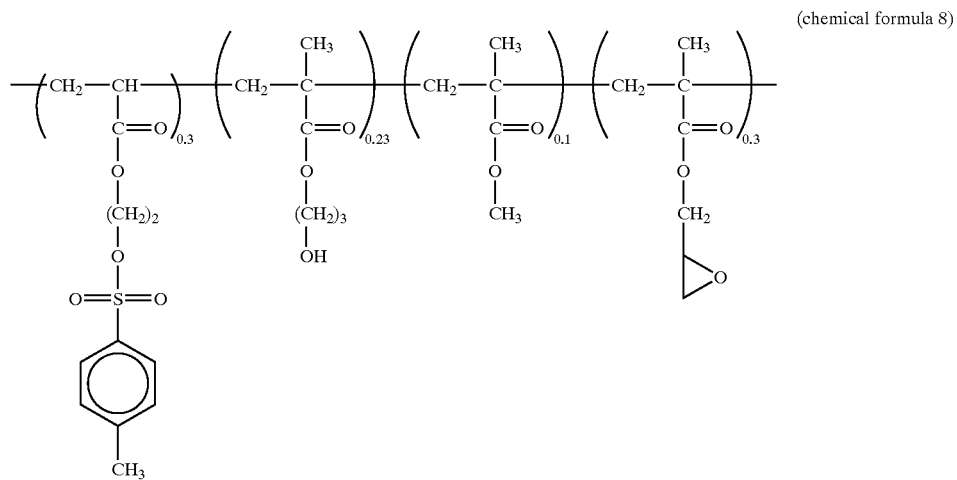

(chemical formula 8)

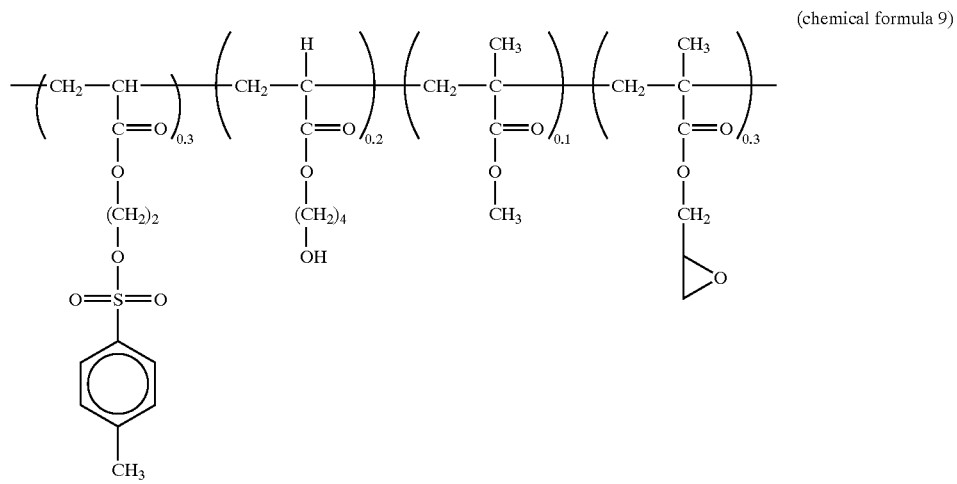

(chemical formula 9)

EXAMPLE X

Synthesis of poly [2-(toluene-4-sulfonyloxy)ethyl methacrylate/2-hydroxyethyl acrylate/-methyl methacrylate/-glycidyl methacrylate]

In a 500 ml round-bottom flask was placed 0.3 mole of 2-(toluene-4-sulfonyloxy)ethyl methacrylate, 0.25 mole of 2-hydroxyethyl acrylate, 0.15 mole of methyl methacrylate, 0.3 mole of glycidyl methacrylate, 300 g of tetrahydrofuran (THF), and 0.1 g–3 g of 2,2-azobisisobutyronitrile (AIBN). The reaction mixture was heated at 60–75° C. for 5–20 hours. The product was precipitated in ethyl ether or n-hexan, filtered and dried to provide poly [2-(toluene-4-sulfonyloxy)ethyl methacrylate/2-hydroxyethyl acrylate/-methyl methacrylate/-glycidyl methacrylate] represented by the following chemical formula 10, at a yield of 65–70%.

EXAMPLE XI

Synthesis of the poly [2-(toluene-4-sulfonyloxy) ethyl methacrylate/2-hydroxyethyl methacrylate-/methyl acrylate-/glycidyl methacrylate]

In a 500 ml round-bottom flask was placed 0.3 mole of 2-(toluene-4-sulfonyloxy)ethyl methacrylate, 0.2 mole of 2-hydroxyethyl methacrylate, 0.15 mole of methyl acrylate, 0.3 mole of glycidyl methacrylate, 300 g of tetrahydrofuran (THF), and 0.1 g–3 g of AIBN. The reaction mixture was heated at 60–75° C. for 5–20 hours. The product was precipitated in ethylether or n-hexane, filtered and dried to provide poly [2-toluene-4-sulfonyloxy)ethyl methacrylate/ 2-hydroxyethyl methacrylate-/methyl acrylate-/glycidyl methacrylate] represented by the following chemical formula 11, at a yield of 65–70%.

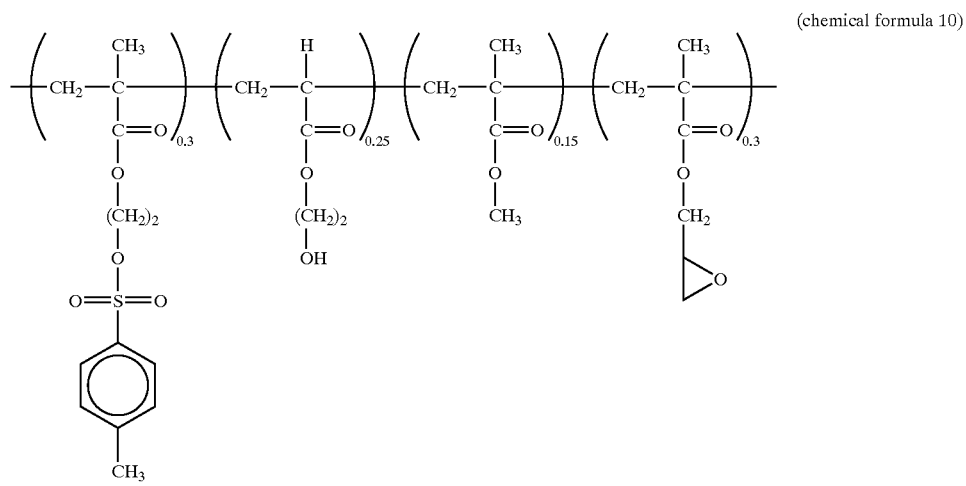

(chemical formula 10)

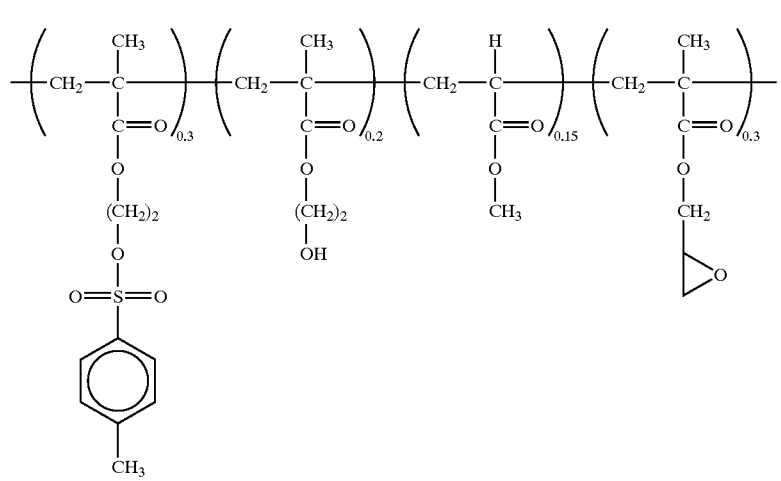

(chemical formula 11)

EXAMPLE XII

Synthesis of poly [2-(toluene-4-sulfonyloxy) ethyl methacrylate/3-hydroxypropyl acrylate-/methyl methacrylate-/glycidyl methacrylate]

In a 500 ml round-bottom flask was placed 0.3 mole of 2-(toluene-4-sulfonyloxy)ethyl methacrylate, 0.25 mole of 3-hydroxypropyl acrylate, 0.15 mole of methyl methacrylate, 0.3 mole of glycidyl methacrylate, 300 g of tetrahydrofuran (THF), and 0.1 g–3 g of AIBN. The reaction mixture was heated at 60–75° C. for 5–20 hours. The product was precipitated in ethyl ether or n-hexane, filtered and dried to provide poly [2-(toluene-4-sulfonyloxy)ethyl methacrylate/3-hydroxypropyl acrylate-/methyl methacrylate-/glycidyl methacrylate] represented by the following chemical formula 12, at a yield of 65–70%.

EXAMPLE XIII

Synthesis of poly [2-(toluene-4-sulfonyloxy)ethyl methacrylate/3-hydroxypropyl methacrylate-/methyl methacrylate-/glycidyl methacrylate]

In a 500 ml round-bottom flask was placed 0.3 mole of 2-(toluene-4-sulfonyloxy)ethyl methacrylate, 0.22 mole of 3-hydroxypropyl methacrylate, 0.15 mole of methyl methacrylate, 0.3 mole of glycidyl methacrylate, 300 g of tetrahydrofuran (THF), and 0.1 g–3 g of AIBN. The reaction mixture was heated at 60–75° C. for 5–20 hours. The product was precipitated in ethyl ether or n-hexane, filtered and dried to provide poly [2-(toluene-4-sulfonyloxy)ethyl methacrylate/3-hydroxypropyl methacrylate-/methyl methacrylate-/glycidyl methacrylate] represented by the following chemical formula 13, at a yield of 65–70%.

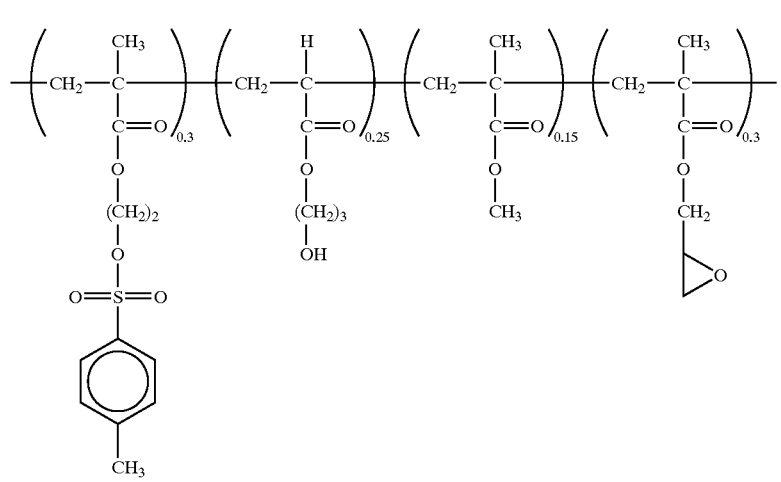

(chemical formula 12)

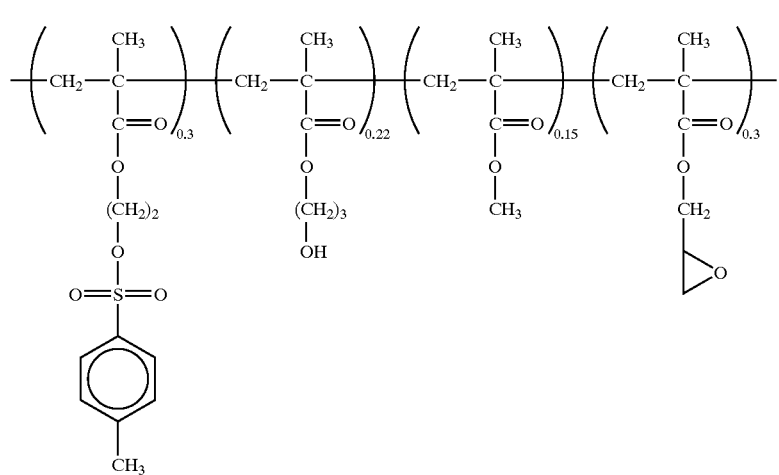

(chemical formula 13)

EXAMPLE XIV

Synthesis of poly [2-(toluene-4-sulfonyloxy)ethyl methacrylate/4-hydroxybutyl acrylate-/methyl methacrylate-/glycidyl methacrylate]

In a 500 ml round-bottom flask was placed 0.3 mole of 2-(toluene-4-sulfonyloxy)ethyl methacrylate, 0.2 mole of 4-hydroxybutyl acrylate, 0.1 mole of methyl methacrylate, 0.3 mole of glycidyl methacrylate, 300 g of tetrahydrofuran (THF), and 0.1 g–3 g of AIBN. The reaction mixture was heated at 60–75° C. for 5–20 hours. The product was precipitated in ethyl ether or n-hexane, filtered and dried to provide poly [2-(toluene-4-sulfonyloxy)ethyl methacrylate/ 4-hydroxybutyl acrylate-/methyl methacrylate-/glycidyl methacrylate] represented by the following chemical formula 14, at a yield of 65–70%.

EXAMPLE XV

Synthesis of poly [2-(toluene-4-sulfonyloxy)ethyl acrylate/2-hydroxyethyl acrylate-/methyl methacrylate]

In a 500 ml round-bottom flask was placed 0.3 mole of 2-(toluene-4-sulfonyloxy)ethyl acrylate, 0.3 mole of 2-hydroxyethyl acrylate, 0.25 mole of methyl methacrylate, 300 g of tetrahydrofuran (THF), and 0.1 g–3 g of AIBN. The reaction mixture was heated at 60–75° C. for 5–20 hours. The product was precipitated in ethyl ether or n-hexane, filtered and dried to provide poly [2-(toluene-4-sulfonyloxy) ethyl acrylate/2-hydroxyethyl acrylate-/methyl methacrylate] represented by the following chemical formula 15, at a yield of 65–70%.

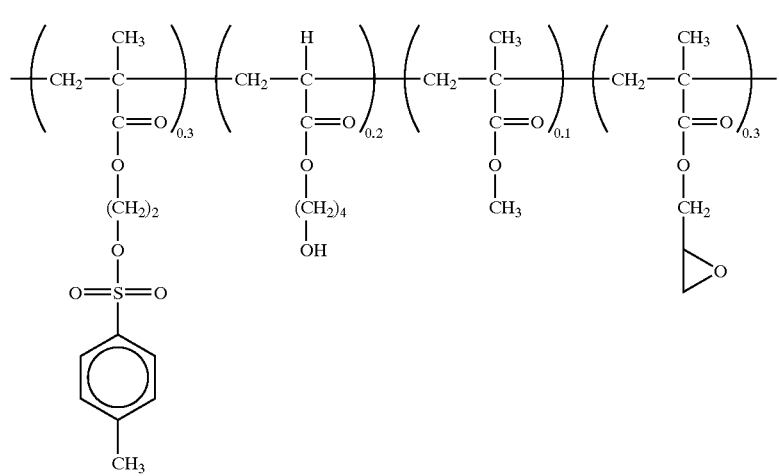

(chemical formula 14)

(chemical formula 15)

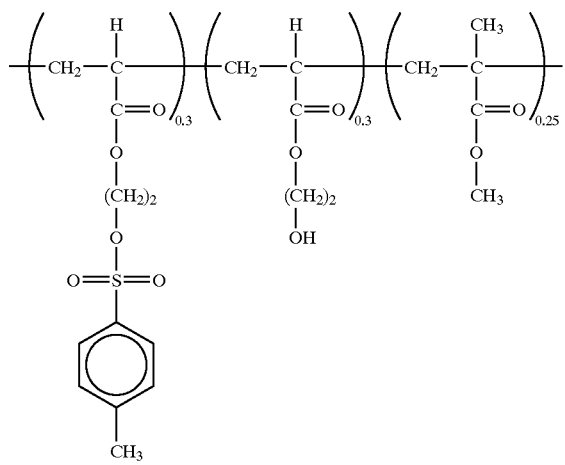

EXAMPLE XVI

Synthesis of poly [2-(toluene-4-sulfonyloxy)ethyl acrylate/2-hydroxyethyl methacrylate-/methyl methacrylate]

In a 500 ml round-bottom flask was placed 0.33 mole of 2-(toluene-4-sulfonyloxy)ethyl acrylate, 0.35 mole of 2-hydroxyethyl methacrylate, 0.25 mole of methyl methacrylate, 300 g of tetrahydrofuran (THF), and 0.1 g–3 g of AIBN. The reaction mixture was heated at 60–75° C. for 5–20 hours. The product was precipitated in ethyl ether or n-hexane, filtered and dried to provide poly [2-(toluene-4-sulfonyloxy)ethyl acrylate/2-hydroxyethyl methacrylate/-methyl methacrylate] represented by the following chemical formula 16, at a yield of 65–70%.

(chemical formula 16)

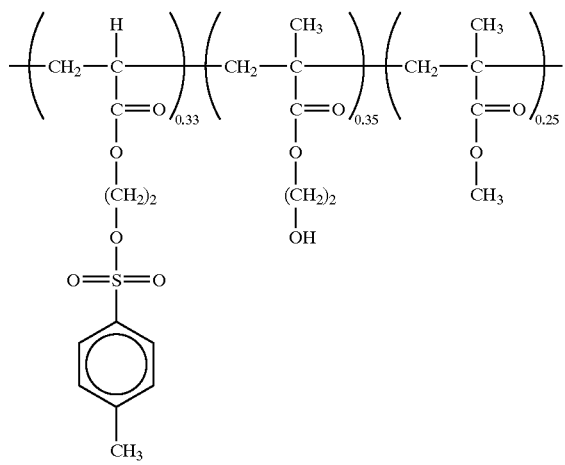

EXAMPLE XVII

Synthesis of poly [2-(toluene-4-sulfonyloxy)ethyl acrylate/3-hydroxypropyl acrylate-/methyl methacrylate]

In a 500 ml round-bottom flask was placed 0.3 mole of 2-(toluene-4-sulfonyloxy)ethyl acrylate, 0.33 mole of 3-hydroxypropyl acrylate, 0.22 mole of methyl methacrylate, 300 g of tetrahydrofuran (THF), and 0.1 g–3 g of AIBN. The reaction mixture was heated at 60–75° C. for 5–20 hours. The product was precipitated in ethyl ether or n-hexane, filtered and dried to provide poly [2-(toluene-4-sulfonyloxy)ethyl acrylate/3-hydroxypropyl acrylate/-methyl methacrylate] represented by the following chemical formula 17, at a yield of 65–70%.

(chemical formula 17)

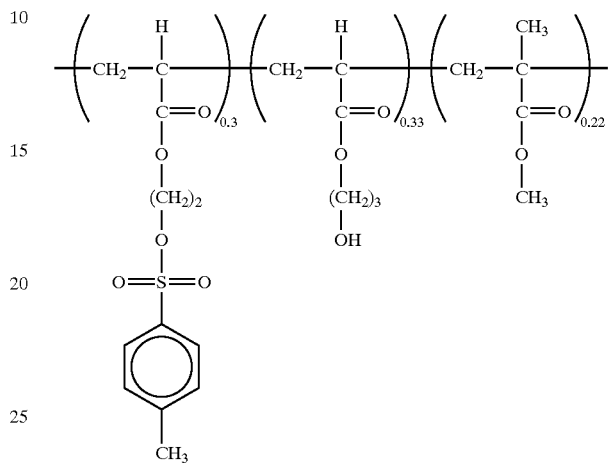

EXAMPLE XVIII

Synthesis of poly [2-(toluene-4-sulfonyloxy)ethyl acrylate/3-hydroxypropyl methacrylate-/methyl methacrylate]

In a 500 ml round-bottom flask was placed 0.3 mole of 2-(toluene-4-sulfonyloxy)ethyl acrylate, 0.33 mole of 3-hydroxypropyl methacrylate, 0.25 mole of methyl methacrylate, 300 g of tetrahydrofuran (THF), and 0.1 g–3 g of AIBN. The reaction mixture was heated at 60–75° C. for 5–20 hours. The product was precipitated in ethyl ether or n-hexane, filtered and dried to provide poly [2-(toluene-4-sulfonyloxy)ethyl acrylate/3-hydroxypropyl methacrylate-/methyl methacrylate] represented by the following chemical formula 18, at a yield of 65–70%.

(chemical formula 18)

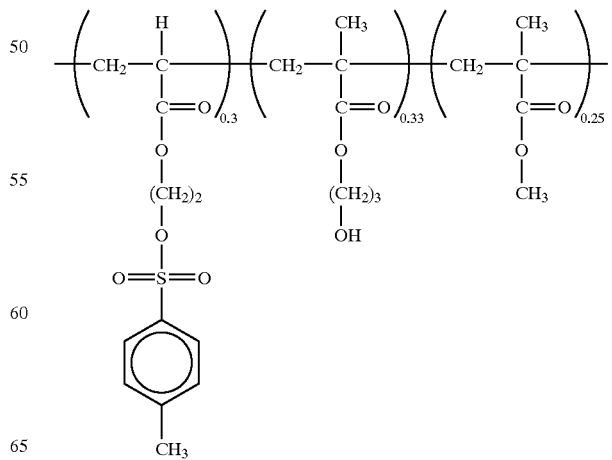

EXAMPLE XIX

Synthesis of poly [2-(toluene-4-sulfonyloxy)ethyl acrylate/4-hydroxybutyl acrylate-/methyl methacrylate]

In a 500 ml round-bottom flask was placed 0.3 mole of 2-(toluene-4-sulfonyloxy)ethyl acrylate, 0.3 mole of 4-hydroxybutyl acrylate, 0.3 mole of methyl methacrylate, 300 g of tetrahydrofuran (THF), and 0.1 g–3 g of AIBN. The reaction mixture was heated at 60–75° C. for 5–20 hours. The product was precipitated in ethyl ether or n-hexane, filtered and dried to provide poly [2-(toluene-4-sulfonyloxy) ethyl acrylate/4-hydroxybutyl acrylate/-methyl methacrylate] represented by the following chemical formula 19, at a yield of 65–70%.

(chemical formula 19)

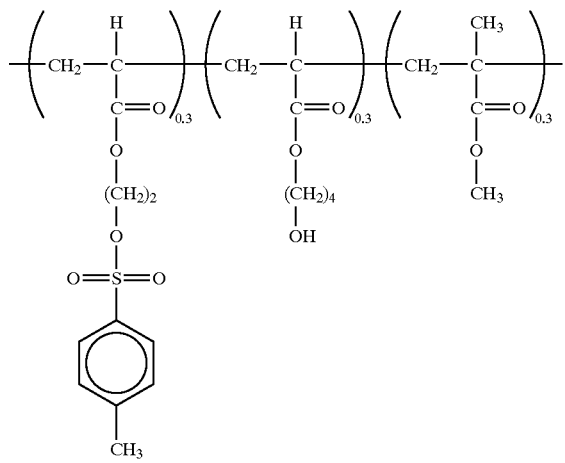

EXAMPLE XX

Synthesis of poly [2-(toluene-4-sulfonyloxy)ethyl methacrylate/2-hydroxyethyl acrylate-/methyl methacrylate]

In a 500 ml round-bottom flask was placed 0.3 mole of 2-(toluene-4-sulfonyloxy)ethyl methacrylate, 0.25 mole of 2-hydroxyethyl acrylate, 0.3 mole of methyl methacrylate, 300 g of tetrahydrofuran (THF), and 0.1 g–3 g of AIBN. The reaction mixture was heated at 60–75° C. for 5–20 hours. The product was precipitated in ethyl ether or n-hexane, filtered and dried to produce poly [2-(toluene-4-sulfonyloxy)ethyl methacrylate/2-hydroxyethyl acrylate-/methyl methacrylate] represented by the following chemical formula 20, at a yield of 65–70%.

(chemical formula 20)

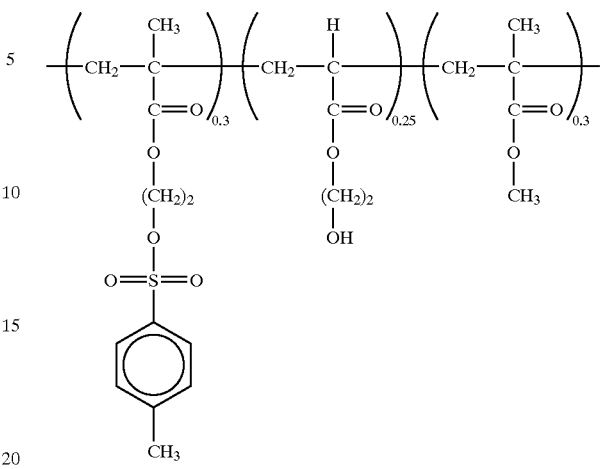

EXAMPLE XXI

Synthesis of poly [2-(toluene-4-sulfonyloxy)ethyl methacrylate/2-hydroxyethyl methacrylate-/methyl methacrylate]

In a 500 ml round-bottom flask was placed 0.3 mole of 2-(toluene-4-sulfonyloxy)ethyl methacrylate, 0.32 mole of 2-hydroxyethyl methacrylate, 0.3 mole of methyl methacrylate, 300 g of tetrahydrofuran (THF), and 0.1 g–3 g of AIBN. The reaction mixture was heated at 60–75° C. for 5–20 hours. The product was precipitated in ethyl ether or n-hexane, filtered and dried to provide poly [2-(toluene-4-sulfonyloxy)ethyl methacrylate/2-hydroxyethyl methacrylate/-methyl methacrylate] represented by the following chemical formula 21, at a yield of 65–70%.

(chemical formula 21)

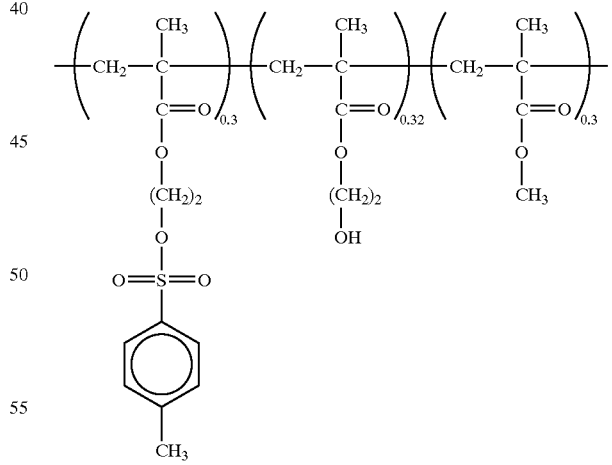

EXAMPLE XXII

Synthesis of poly [2-(toluene-4-sulfonyloxy) ethyl methacrylate/3-hydroxypropyl acrylate/-methyl methacrylate]

In a 500 ml round-bottom flask was placed 0.3 mole of 2-(toluene-4-sulfonyloxy)ethyl methacrylate, 0.33 mole of 3-hydroxypropyl acrylate, 0.3 mole of methyl methacrylate, 300 g of tetrahydrofuran (THF), and 0.1 g–3 g of AIBN. The reaction mixture was heated at 60–75° C. for 5–20 hours. The product was precipitated in ethyl ether or n-hexane, filtered and dried to provide poly [2-(toluene-4-sulfonyloxy) ethyl methacrylate/3-hydroxypropyl acrylate/-methyl methacrylate] represented by the following chemical formula 22, at a yield of 65–70%.

(chemical formula 22)

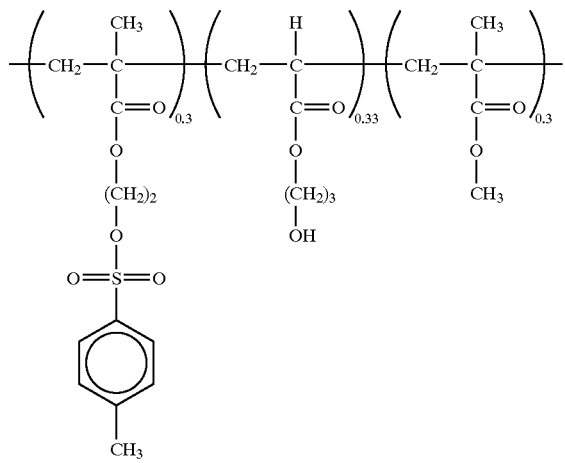

EXAMPLE XXIII

Synthesis of poly [2-(toluene-4-sulfonyloxy)ethyl methacrylate/3-hydroxypropyl methacrylate-/methyl methacrylate]

In a 500 ml round-bottom flask was placed 0.3 mole of 2-(toluene-4-sulfonyloxy)ethyl methacrylate, 0.3 mole of 3-hydroxypropyl methacrylate, 0.3 mole of methyl methacrylate, 300 g of tetrahydrofuran (THF), and 0.1 g–3 g of AIBN. The reaction mixture was heated at 60–75° C. for 5–20 hours. The product was precipitated in ethyl ether or n-hexane, filtered and dried to produce poly [2-(toluene-4-sulfonyloxy)ethyl methacrylate/3-hydroxypropyl methacrylate/-methylmeth acrylate] represented by the following chemical formula 23, at a yield of 65–70%.

(chemical formula 23)

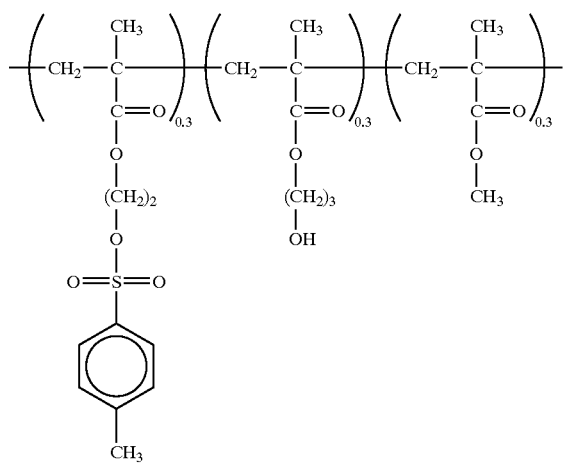

EXAMPLE XXIV

Synthesis of poly [2-(toluene-4-sulfonyloxy)ethyl methacrylate/4-hydroxybutyl acrylate-/methyl methacrylate]

In a 500 ml round-bottom flask was placed 0.3 mole of 2-(toluene-4-sulfonyloxy) acrylate, 0.33 mole of 4-hydroxybutyl acrylate, 0.3 mole of methyl methacrylate, 300 g of tetrahydrofuran (THF), and 0.1 g–3 g of AIBN. The reaction mixture was heated at 60–75° C. for 5–20 hours. The product was precipitated in ethyl ether or n-hexane, filtered and dried to provide poly [2-(toluene-4-sulfonyloxy) ethyl acrylate/4-hydroxybutyl acrylate/-methyl methacrylate] represented by the following chemical formula 24, at a yield of 65–70%.

(chemical formula 24)

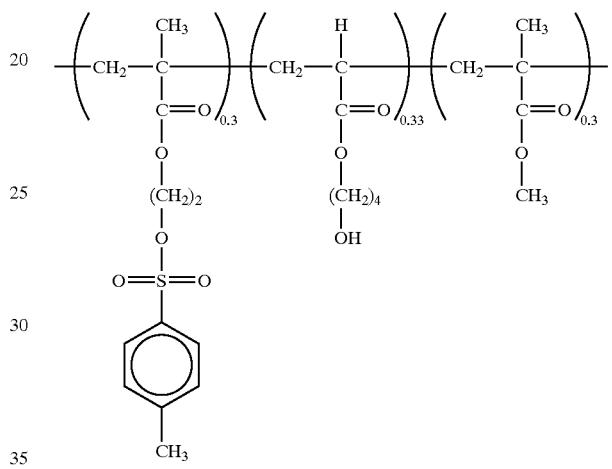

EXAMPLE XXV

Preparation of ARC

A polymer (resin) having a chemical structure of general formula 1, as obtained in each of Examples V–XIV polymer (resin), is dissolved in 200–5,000% (w/w) of propyleneglycolmethyletheracetate (PGMEA). This solution is filtered, coated on a wafer, and hard-baked (i.e. heated at 100–300° C. for 10–1,000 sec). A photosensitive material may be applied on the anti-reflective coating thus formed, and imaged to ultrafine patterns in the conventional manner.

EXAMPLE XXVI

Preparation of ARC

A polymer (resin) having a chemical structure of the general formula 2, as obtained in each of Examples XV–XXIV is dissolved in 200–5,000% (w/w) of propyleneglycolmethyletheracetate (PGMEA). This solution, alone or in combination with 0.1–30% by weight of at least one cross-linker selected from the group consisting of acroleindimethylacetal, acroleindiethylacetal and melamine type cross-linker is filtered, coated on a wafer, and hard-baked (i.e. heated at 100–300° C. for 10–1,000 sec). A photosensitive material may be applied on the anti-reflective coating thus formed, and imaged to ultrafine patterns in the conventional manner.

As described hereinbefore, anti-reflective coating of the present invention, for example, coatings formed from the polymer resins of chemical formulas 5 to 24, contain phenyl groups pendant from the polymeric backbone which exhibit superior absorbency at 193 nm wavelength. Thus, an anti-reflective coating of the present invention can play an excellent role in forming ultrafine patterns. For example, it can prevent the back-reflection of light from the wafer surface and lower layers as well as eliminate the standing waves in the photoresist layer itself during a submicrolithographic process using a 193 nm ArF laser. This results in the formation of ultrafine patterns suitable for 64 M, 256 M, 1 G, 4 G, and 16 G DRAM semiconductor devices and a great improvement in the production yield.

What is claimed is:

1. A polymer derived from a monomer mixture comprising:

(a) compound of the formula:

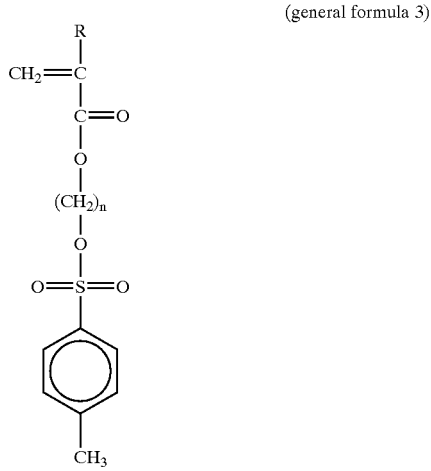

(general formula 3)

wherein,

R is hydrogen or methyl group; and n is 2 or 3;

(b) a hydroxyalkyl acrylate; and (c) an alkyl acrylate.

2. A polymer represented by the following general formula 1:

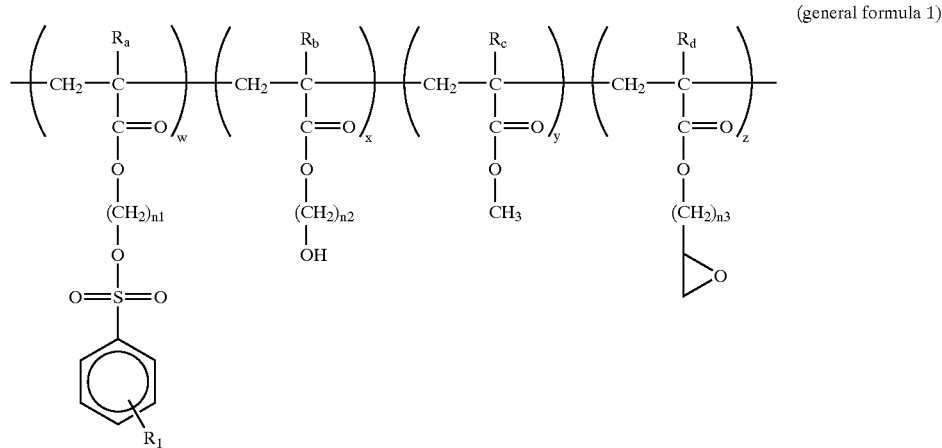

(general formula 1)

wherein, $R_a$, $R_b$, $R_c$ and $R_d$ each represents hydrogen or methyl group; $R_1$ represents hydrogen, hydroxy, a substituted or unsubstituted, straight or branched alkyl of $C_1$–$C_5$, cycloalkyl, alkoxyalkyl or cycloalkoxyalkyl; w, x, y and z each represents a mole fraction of 0.01–0.99; and $n_1$, $n_2$ and $n_3$ each represents an integer of 1 to 4.

3. A polymer as set forth in claim 2 wherein $R_1$ represents methyl.

4. A polymer as set forth in claim 3 comprising—poly [2-(toluene sulfonyloxy)ethyl acrylate/-hydroxyethyl acrylate/-methyl methacrylate/-glycidyl methacrylate] wherein the mole ratio of 2-(toluene sulfonyloxy)ethyl acrylate:hydroxyethyl acrylate:methyl methacrylate:glycidyl methacrylate is 0.3:0.25:0.1:0.3.

5. A polymer as set forth in claim 3 comprising poly [2-(toluene sulfonyloxy)ethyl acrylate/-hydroxyethyl methacrylate/-methyl methacrylate/-glycidyl methacrylate] wherein the mole ratio of 2-(toluene sulfonyloxy)ethyl acrylate:hydroxyethyl methacrylate:methyl methacrylate:glycidyl methacrylate is 0.3:0.2:0.1:0.3.

6. A polymer as set forth in claim 3 comprising poly [2-(toluene sulfonyloxy)ethyl acrylate/-hydroxypropyl acrylate/-methyl methacrylate/-glycidyl methacrylate] wherein the mole ratio of 2-(toluene sulfonyloxy)ethyl acrylate:hydroxypropyl acrylate:methyl methacrylate:glycidyl methacrylate is 0.3:0.25:0.1:0.3.

7. A polymer as set forth in claim 3 comprising—poly [2-(toluene sulfonyloxy)ethyl acrylate/-hydroxypropyl methacrylate/-methyl methacrylate/-glycidyl methacrylate] wherein the mole ratio of 2-(toluene sulfonyloxy)ethyl acrylate:hydroxypropyl methacrylate:methyl methacrylate:glycidyl methacrylate is 0.3:0.23:0.1:0.3.

8. A polymer as set forth in claim 3 comprising—poly [2-(toluene sulfonyloxy)ethyl acrylate/-hydroxybutyl acrylate/-methyl methacrylate/-glycidyl methacrylate] wherein the mole ratio of 2-(toluene sulfonyloxy)ethyl acrylate:hydroxybutyl acrylate:methyl methacrylate:glycidyl methacrylate is 0.3:0.2:0.1:0.3.

9. A polymer as set forth in claim 3 comprising—poly [2-(toluene sulfonyloxy)ethyl methacrylate/-hydroxyethyl acrylate/-methyl methacrylate/-glycidyl methacrylate] wherein the mole ratio of 2-(toluene sulfonyloxy)ethyl methacrylate:hydroxyethyl acrylate:methyl methacrylate:glycidyl methacrylate is 0.3:0.25:0.15:0.3.

10. A polymer as set forth in claim 3 comprising—poly [2-(toluene sulfonyloxy)ethyl methacrylate/-hydroxyethyl methacrylate/-methyl acrylate/-glycidyl methacrylate] wherein the mole ratio of 2-(toluene sulfonyloxy)ethyl methacrylate:hydroxy ethyl acrylate:methyl acrylate:glycidyl methacrylate is 0.3:0.2:0.15:0.3.

11. The polymer as set forth in claim 3 comprising—poly [2-(toluene sulfonyloxy)ethyl methacrylate/-hydroxypropyl acrylate/-methyl methacrylate/-glycidyl methacrylate]

wherein the mole ratio of 2-(toluene sulfonyloxy)ethyl methacrylate:-hydroxypropyl acrylate:methyl methacrylate:glycidyl methacrylate is 0.3:0.25:0.15:0.3.

12. A polymer as set forth in claim 3 comprising—poly[2-(toluene sulfonyloxy)ethyl methacrylate/-hydroxypropyl methacrylate/-methyl methacrylate/-glycidyl methacrylate] wherein the mole ratio of 2-(toluene sulfonyloxy)ethyl methacrylate/:hydroxypropyl methacrylate:methyl methacrylate:glycidyl methacrylate is 0.3:0.22:0.15:0.3.

13. A polymer as set forth in claim 3 comprising—poly[2-(toluene sulfonyloxy)ethyl methacrylate/-hydroxybutyl acrylate/-methyl methacrylate/-glycidyl methacrylate] wherein the mole ratio of 2-(toluene sulfonyloxy)ethyl methacrylate:hydroxybutyl acrylate:methyl methacrylate:glycidyl methacrylate is 0.3:0.2:0.1:0.3.

14. A method for preparing the polymer of claim 2 comprising polymerizing a (toluene sulfonyloxy)alkyl acrylate-type monomer, a hydroxyalkyl acrylate-type monomer, an alkyl acrylate-type monomer and a glycidyl methacrylate-type monomer in the presence of an initiator, as shown in the following reaction equation 1:

(reaction equation 1)

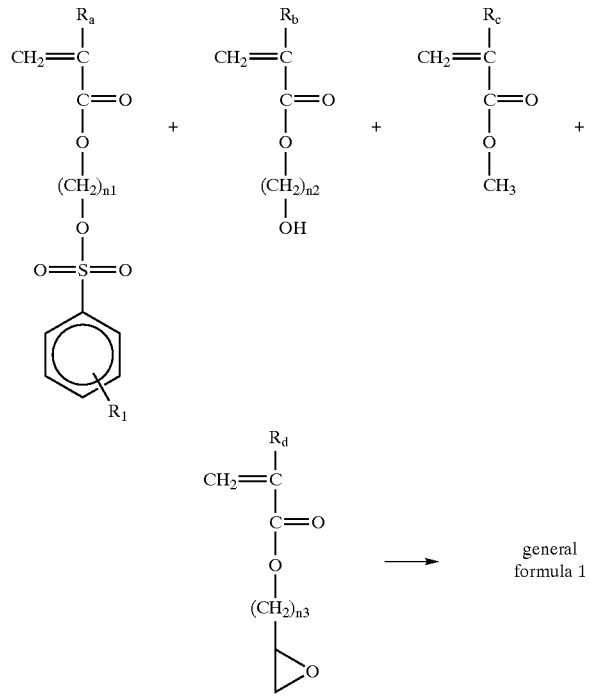

general formula 1 wherein,
$R_a$, $R_b$, $R_c$ and $R_d$ each represents hydrogen or methyl group; $R_1$ represents hydrogen, hydroxy, a substituted or unsubstituted, straight or branched alkyl of $C_1$–$C_5$, cycloalkyl, alkoxyalkyl or cycloalkoxyalkyl; and $n_1$, $n_2$ and $n_3$ each represents an integer of 1 to 4.

15. A method for preparing a polymer according to claim 14, wherein $R_1$ represents methyl.

16. A method for preparing a polymer according to claim 14, wherein the initiator is selected from the group consisting of 2,2-azobisisobutyronitrile (AIBN), acetylperoxide, laurylperoxide and t-butylperoxide.

17. A method for preparing a polymer according to claim 14, further comprising a solvent selected from the group consisting of tetrahydrofuran, toluene, benzene, methylethylketone and dioxane.

18. A method for preparing a polymer according to claim 14, wherein the polymerizing reaction is conducted at 50–80° C.

19. A polymer represented by the following general formula 2:

(general formula 2)

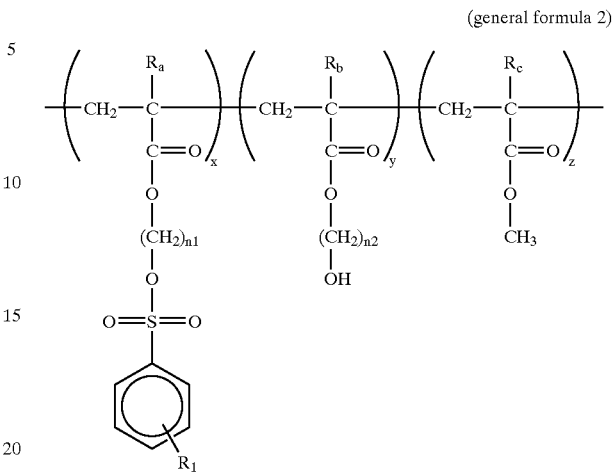

wherein,
$R_a$, $R_b$ and $R_c$ each represents hydrogen or methyl group; $R_1$ represents hydrogen, hydroxy, straight or branched alkyl of $C_1$–$C_5$, cycloalkyl, alkoxyalkyl or cycloalkoxyalkyl; x, y and z each represents mole fraction of 0.01–0.99; and $n_1$ and $n_2$ each represents an integer of 1 to 4.

20. A polymer as set forth in claim 19 wherein $R_1$ represents methyl.

21. A polymer as set forth in claim 20 comprising poly[2-(toluene sulfonyloxy)ethyl acrylate/-hydroxyethyl acrylate/-methyl methacrylate] wherein the mole ratio of 2-(toluene sulfonyloxy)ethyl acrylate:hydroxyethyl acrylate:methyl methacrylate is 0.3:0.3:0.25.

22. A polymer as set forth in claim 20 comprising poly[2-(toluene sulfonyloxy)ethyl acrylate/-hydroxyethyl methacrylate/-methyl methacrylate] wherein the mole ratio of 2-(toluene sulfonyloxy)ethyl acrylate:hydroxyethyl methacrylate:methyl methacrylate is 0.33:0.35:0.25.

23. A polymer as set forth in claim 20 comprising poly[2-(toluene sulfonyloxy)ethyl acrylate/-hydroxypropyl acrylate/-methyl methacrylate] wherein the mole ratio of 2-(toluene sulfonyloxy)ethyl acrylate:hydroxypropyl acrylate:methyl methacrylate is 0.3:0.33:0.22.

24. A polymer as set forth in claim 20 comprising poly[2-(toluene sulfonyloxy)ethyl acrylate/-hydroxypropyl methacrylate-/methyl methacrylate] wherein the mole ratio of 2-(toluene sulfonyloxy)ethyl acrylate:hydroxypropyl methacrylate:methyl methacrylate is 0.3:0.33:0.25.

25. A polymer as set forth in claim 20 comprising poly[2-(toluene sulfonyloxy)ethyl acrylate/-hydroxybutyl acrylate/-methyl methacrylate] wherein the mole ratio of 2toluene sulfonyloxy)ethyl acrylate:hydroxybutyl acrylate-:methyl methacrylate is 0.3:0.3:0.3.

26. A polymer as set forth in claim 20 comprising poly[2-(toluene sulfonyloxy)ethyl methacrylate/-hydroxyethyl acrylate/-methyl methacrylate] wherein the mole ratio of 2-(toluene sulfonyloxy)ethyl methacrylate:hydroxyethyl acrylate:methyl methacrylate is 0.3:0.25:0.3.

27. A polymer as set forth in claim 20 comprising poly[2-(toluene sulfonyloxy)ethyl methacrylate/-hydroxyethyl methacrylate-/methyl methacrylate] wherein the mole ratio of 2-(toluene sulfonyloxy)ethyl methacrylate:hydroxyethyl methacrylate:methyl methacrylate is 0.3:0.32:0.3.

28. A polymer as set forth in claim 20 comprising poly[2-(toluene sulfonyloxy)ethyl methacrylate/-hydroxypropyl acrylate/-methyl methacrylate] wherein the mole ratio of 2-(toluene sulfonyloxy)ethyl methacrylate:hydroxypropyl acrylate:methyl methacrylate is 0.3:0.33:0.3.

29. A polymer as set forth in claim 20 comprising poly [2-(toluene sulfonyloxy)ethyl methacrylate/-hydroxypropyl methacrylate/-methyl methacrylate] wherein the mole ratio of 2-(toluene sulfonyloxy)ethyl methacrylate:hydroxypropyl methacrylate:methyl methacrylate is 0.3:0.3:0.3.

30. A polymer as set forth in claim 20 comprising poly [2-(toluene sulfonyloxy)ethyl methacrylate/-hydroxybutyl acrylate/-methyl methacrylate]—wherein the mole ratio of 2-(toluene sulfonyloxy)ethyl methacrylate:hydroxybutyl acrylate:methyl methacrylate is 0.3:0.33:0.3.

31. A method for preparing a polymer of claim 19 comprising polymerizing toluene sulfonyloxy)alkyl acrylate-type monomer, a hydroxyalkyl acrylate-type monomer and an alkyl acrylate-type monomer in the presence of an initiator as shown in the following reaction equation 2:

(reaction equation 2)

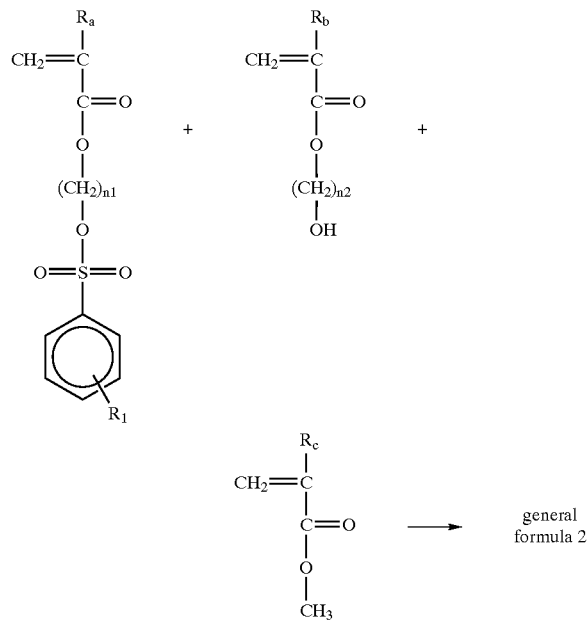

general formula 2 wherein,
$R_a$, $R_b$ and $R_c$ each represents hydrogen or methyl group; $R_1$ represents hydrogen, hydroxy, a substituted or unsubstituted, straight or branched alkyl of $C_1$–$C_5$, cycloalkyl, alkoxyalkyl or cycloalkoxyalkyl; and $n_1$ and $n_2$ each represents an integer of 1 to 4.

32. A method for preparing a polymer as set forth in claim 31, wherein $R_1$ represents methyl.

33. A method for preparing a polymer as set forth in claim 31, wherein the initiator is selected from the group consisting of 2,2-azobisisobutyronitrile (AIBN), acetylperoxide, laurylperoxide and t-butylperoxide.

34. A method for preparing a polymer as set forth in claim 31, further comprising a solvent selected from the group consisting of tetrahydrofuran, toluene, benzene, methylethylketone and dioxane.

35. A method for preparing a polymer as set forth in claim 31, wherein the polymerizing reaction is conducted at 50–80° C.

36. An anti-reflective coating comprising the polymer of claim 2.

37. A method for preparing an anti-reflective coating, which comprises dissolving 200–5000% (w/w) of the polymer of claim 2 in an organic solvent to form a coating composition; coating said composition on a wafer; and subjecting the coated wafer to hard baking for 10 to 1000 sec. at 100–300° C.

38. A method as set forth in claim 37, wherein the organic solvent is selected from the group consisting of ethyl 3-ethoxypropionate, methyl 3-methoxypropionate, cyclohexanone and propyleneglycolmethyletheracetate.

39. An anti-reflective coating comprising the polymer of claim 19 and an additive selected from the group consisting of acroleindimethylacetal, acroleindiethylacetal and melamine-type crosslinkers.

40. A method for preparing anti-reflective coating useful in fabricating semiconductor devices which comprises dissolving 200–5000% (w/w) of the polymer of claim 19 in a organic solvent; dissolving therein an additive selected from the group consisting of acroleindimethylacetal, acroleindiethylacetal and melamine type cross-linkers to form a coating composition; filtering said composition, coating said composition on a wafer; and subjecting the coated wafer to hard baking for 10 to 1000 sec. at 100–300° C.

41. A method as set forth in claim 40, wherein the organic solvent is selected from the group consisting of ethyl 3-ethoxypropionate, methyl 3-methoypropionate, cyclohexanone and propyleneglycolmethyletheracetate.

42. A method as set forth in claim 40, wherein said additive is used at an amount of 0.1 to 30% (w/w).

43. A method as set forth in claim 40, wherein said additive is used at an amount of 0.1 to 30% (w/w).

44. A semiconductor device comprising the anti-reflective coating of claim 39.

* * * * *